(12) United States Patent
Groenewegen et al.

(10) Patent No.: US 6,931,273 B2
(45) Date of Patent: Aug. 16, 2005

(54) DATABASE OF BODY SURFACE ECG P WAVE INTEGRAL MAPS FOR LOCALIZATION OF LEFT-SIDED ATRIAL ARRHYTHMIAS

(75) Inventors: Arne Sippens Groenewegen, Burlingame, CA (US); Michael D. Mlynash, Moutain View, CA (US)

(73) Assignee: University of California San Francisco, San Francisco, CA (US)

(*) Notice: Subject to any disclaimer, the term of this patent is extended or adjusted under 35 U.S.C. 154(b) by 974 days.

(21) Appl. No.: 09/835,125

(22) Filed: Apr. 11, 2001

(65) Prior Publication Data

US 2002/0026220 A1 Feb. 28, 2002

Related U.S. Application Data

(60) Provisional application No. 60/196,204, filed on Apr. 11, 2000.

(51) Int. Cl.[7] .............................................. A61B 5/04
(52) U.S. Cl. ...................................... 600/515; 600/509
(58) Field of Search .............................. 600/509, 515, 600/516, 518

(56) References Cited

U.S. PATENT DOCUMENTS

| | | | |
|---|---|---|---|
| 4,550,502 A | 11/1985 | Grayzel | 33/1 B |
| 4,721,114 A | 1/1988 | Dufault et al. | 128/696 |
| 5,313,953 A | 5/1994 | Yomtov et al. | 128/696 |
| 5,609,158 A | 3/1997 | Chan | 128/705 |
| 5,818,570 A | 10/1998 | Urbanczyk | 355/75 |
| 5,840,038 A | 11/1998 | Xue et al. | 600/512 |
| 6,038,476 A | 3/2000 | Schwartz | 607/27 |

Primary Examiner—Carl Layno
(74) Attorney, Agent, or Firm—Lumen Intellectual Property Services, Inc.

(57) ABSTRACT

A system and method are provided for developing a database of body surface ECG P-wave maps for classification and localization of left-sided atrial arrhythmias. The system and method include generating and receiving P-wave data in a subject by left atrial pacing or receiving P-wave data in a subject during spontaneously occurring or induced left atrial arrhythmias; computing (e.g. potential or integral) maps of the P-wave data; classifying the maps specific to a left atrial ectopic origin; verifying the classification procedure; averaging the classified maps into mean maps; and storing and accessing the mean maps in the database. The mean maps of the P-wave data in the database can be used to automatically classify and localize P-wave data from a patient obtained during a left atrial arrhythmia such as atrial tachycardia, focal atrial fibrillation, or orthodromic atrioventricular reentrant tachycardia.

91 Claims, 11 Drawing Sheets

⊕ 5.7 mVms
⊖ 2.9 mVms

P Wave Integral

DATABASE OF BODY SURFACE ECG P WAVE INTEGRAL MAPS FOR LOCALIZATION OF LEFT-SIDED ATRIAL ARRHYTHMIAS

CROSS-REFERENCE TO RELATED APPLICATIONS

This application is based on Provisional application 60/196,204 filed Mar. 11, 2000 which is herein incorporated by reference. This application cross-references to Non-provisional application 09/809,719 filed Mar. 14, 2001, Non-provisional application 09/808,728 filed Mar. 14, 2001, Non-provisional application 09/724,947 filed Nov. 28, 2000, all of which are herein incorporated by reference.

STATEMENT REGARDING FEDERALLY SPONSORED RESEARCH OR DEVELOPMENT

This invention was supported in part by grants from the National Institutes of Health under grant number HL09602 and RO1-HL55027. The government has certain rights in the invention.

FIELD OF THE INVENTION

This invention relates generally to a method for classification and localization of arrhythmias. More particularly, the present invention relates to a system for developing a database of body surface electrocardiogram (ECG) P wave data maps for localization of the origin of left-sided atrial arrhythmias.

BACKGROUND ART

Early investigations utilizing atrial pacing in man to study the variations in scalar ECG morphology and vector loop of the P wave with varying sites of focal atrial origin, were primarily geared towards the differentiation of left- from right-sided atrial rhythms (e.g. Massumi R. A. and Tawakkol A. A. (1967), *Direct study of left atrial P waves, Am. J. Cardiol.* 20:331–340; and Harris B. C. et al. (1968) *Left atrial rhythm; Experimental production in man, Circulation* 37:1000–1014). Despite several attempts to develop a set of morphologic ECG criteria specific to a left-sided origin of an ectopic atrial rhythm, different algorithms were proposed and consensus appeared difficult to attain.

Mirowski in 1967 initially suggested that a negative P wave polarity in lead I and a "dart and dome" configuration in $V_1$ was related to a left-sided origin and later added that a negative P wave in $V_6$ was more specific particularly when the aforementioned features were absent (Mirowski M. (1967) *Ectopic rhythms originating anteriorly in the left atrium; Analysis of 12 cases with P wave inversion in all precordial leads, Am. Heart J.* 74:299–308). Although these findings were partly underlined by others (e.g. Leon D. F. et al. (1970) *Right atrial ectopic rhythms; Experimental production in man, Am. J. Cardiol.* 25:6–10), Harris et al. in 1968 (same reference as mentioned above) contested the importance of P wave inversion in leads I and $V_6$ for a left-sided rhythm and alternatively proposed that a terminally positive P wave in $V_1$ was a more specific finding for a left atrial origin. Conversely, Massumi and Tawakkol (same reference as mentioned above) noted a profound variability in P wave morphology after electrically stimulating the left atrium from similar anatomical sites in different patients and did not believe that distinct ECG criteria specific to areas of ectopic left atrial impulse formation could be developed.

Using temporarily implanted pacing wires following cardiac surgery, Maclean et al. subsequently performed a comprehensive study in 69 patients by stimulating both atria at a total of 12 epicardial regions (Maclean W. A. H. et al. (1975) *P waves during ectopic atrial rhythms in man; A study utilizing atrial pacing with fixed electrodes, Circulation* 52:426–434). Overall the results of this study were disappointing in that only a few specific correlations between P wave morphology and site of origin could be made: (1) a negative P wave in the inferior leads with pacing of the inferior regions in either atrium; (2) a negative P wave in lead I with left atrial pacing near the left pulmonary veins; (3) a positive bifid P wave in $V_1$ with pacing near the lower pulmonary veins and coronary sinus. Therefore, these investigators and recently others using contemporary multisite endocardial catheter mapping techniques (Man K. C. et al. (1996) *Spatial resolution of atrial pace mapping as determined by uniploar atrial pacing at adjacent sites, Circulation* 94:1357–1363), underline the complexity of visual analysis of the low-voltage P wave and concluded that the 12-lead ECG was of limited clinical value in localizing ectopic atrial foci.

The limited role of the standard 12-lead ECG to distinguish right from left atrial focal activity has also been reported by Kalman et al. during ablation of atrial tachycardia guided by intracardiac echocardiography (Kalman J. M. et al. (1998) *"Cristal tachycardias": origin of right atrial tachycardias from the crista terminalis identified by intracardiac echocardiography, J. Am. Coll. Cardiol.* 31:451–459). Kalman et al. reported that the P wave morphology on the 12-lead ECG of tachycardias arising from the upper part of the crista terminalis in the right atrium or the right upper pulmonary vein in the left atrium, demonstrates considerable overlap due to the proximity of both structures. Tang et al. suggested previously that a change in P wave morphology in lead $V_1$ from biphasic during sinus rhythm to completely positive during tachycardia would be helpful in discriminating foci arising from the superior portion of the crista terminalis and the right upper pulmonary vein (Tang C. W. et al. (1995), *Use of P wave configuration during atrial tachycardia to predict site of origin, J. Am. Coll. Cardiol.* 26:1315–1324). The latter finding was found to be predictive for right upper pulmonary vein tachycardia foci even when lead aVL would demonstrate a positive instead of a negative P wave.

There have also been attempts to localize the atrial insertion site of an accessory pathway during orthodromic atrioventricular (AV) reentrant tachycardia. Farshidi et al. initially demonstrated that a negative retrograde P wave in lead I was associated with a left-sided atrial insertion of the accessory pathway (Farshidi A. et al. (1978) *Electrophysiologic characteristics of concealed bypass tracts: clinical and electrocardiographic correlates, Am. J. Cardiol.* 41:1052–1060). Garcia Rivera et al. was able to separate free wall accessory pathway locations in the left and right atrium using the retrograde P wave polarity in leads I and $V_1$ (Garcia Rivera R. et al. (1980) *Retrograde P wave polarity in reciprocating tachycardia utilizing lateral bypass tracts, Eur. Heart J.* 1:137–145). Other investigators have later studied the localization resolution of the 12-lead ECG for this particular application by confining pace mapping to the annular regions of the left and right atrium (e.g. Fitzgerald D. M. et al. (1996) *P wave morphology during atrial pacing along the atrioventricular ring; ECG localization of the site of origin of retrograde atrial activation, J. Electrocardiol.* 29:1–10). However, despite a more directed pace mapping approach, the paced P wave morphology only allowed a gross separation of pacing sites in terms of a left-versus right-sided origin, an inferior origin in either atrium, or an origin in the right free wall. In contrast, Tai et al. recently reported that the polarity of the retrograde P wave in leads I, II, III, aVF, and $V_1$ obtained during AV reentrant tachycardia allows accessory pathway localization to 9 possible annular regions with an overall accuracy of 88% provided a clearly visible P wave could be discriminated (Tai C. T. et al. (1997) *A new electrocardiographic algorithm using retrograde P waves for differentiating atrioventricular node reentrant tachycardia from atrioventricular reciprocating tachycardia mediated by concealed accessory pathway,* J. Am. Coll. Cardiol. 29:394–402). It has also been realized with this application of the surface ECG, that visual analysis of the low-voltage retrograde P wave is frequently hampered by the simultaneous occurrence of the preceding cardiac cycle's high-voltage TU wave.

As mentioned above, visual inspection of the 12-lead ECG in an attempt to correlate changes in P wave morphology and polarity with various locations of ectopic activity is hampered by a low-amplitude signal which is often buried in the preceding TU wave, and also by inter-patient inconsistency in P wave pattern with comparable locations of ectopic left atrial activation, and poor overall spatial resolution in both the left and right atrium. It has been recently demonstrated using right atrial pace mapping that a significantly higher electrocardiographic localization resolution is clinically feasible when multi-lead ECG techniques are adopted (SippensGroenewegen A. et al. (1998) *Body surface mapping during pacing at multiple sites in the human atrium; P wave morphology of ectopic right atrial activation,* Circulation 97:369–380).

There is one preliminary clinical report investigating the use of multi-lead ECG or body surface mapping to discriminate ectopic left atrial activation (Kawano S. and Hiraoka M. P. (1995) *P wave mapping in ectopic atrial rhythm. In: Yasui S. et al. Eds. "Advances in Body Surface Mapping and High Resolution ECG":* Nagoya, Japan: Life Medicom pp. 47–56). Kawano and Hiraoka showed that endocardial pacing at one right (low) and three left (low, middle, and high) atrial locations produced characteristic P wave body surface potential map patterns. Access to the latter left atrial locations was attained exclusively through the coronary sinus. However, only a moderate number of pacing site locations were studied while pacing from the pulmonary veins was not attempted.

It is clear that the development of noninvasive methods for clinical localization of left atrial arrhythmias with sufficient and high electrocardiographic resolution is difficult. Therefore, noninvasive localization of left atrial arrhythmias is in need of alternative methods that enable improved discrimination and differentiation of electrocardiographic P wave patterns or morphologies.

OBJECTIVES AND ADVANTAGES

In light of the above, it is the primary objective of the present invention to provide a system for developing a database of body surface ECG P wave data maps. Body surface ECG mapping can be applied to improve noninvasive localization of left atrial arrhythmias prior to radiofrequency catheter ablation.

It is an additional object of the invention to provide a method of storing a database of mean body surface ECG P wave data maps in a computer-readable medium for retrieval, analysis and sharing.

It is an additional object of the invention to provide a database that will enable detailed noninvasive localization of left atrial arrhythmias so that invasive catheter mapping may be targeted and minimized to a small confined segment of the left atrium prior to ablation therapy delivery.

The advantage of the present invention is that the present invention results in shorter and more efficient mapping and ablation procedures with less fluoroscopic exposure of the patient and physician. Additionally, the patient will undergo less trauma and benefit from reduction in the risk for clot formation and stroke since the time required for catheter manipulation in the left atrium can be significantly reduced.

An additional advantage is that the database can be used in an outpatient clinic or physician's office to noninvasively screen patients and map the arrhythmia's origin before admitting a patient to the electrophysiology laboratory to undergo ablation therapy. This noninvasive diagnosis and screening will also enable improved decision making regarding the optimal choice of therapy, e.g. anti-arrhythmic drugs, permanent pacing, ablation treatment, or combinations of these treatment modalities. Another advantage of the present invention is that it will also allow for noninvasive follow-up of patients with left atrial arrhythmias after therapy delivery to assess arrhythmia recurrences due to treatment failure or disease progression.

SUMMARY

The present invention provides a method for classification and localization of arrhythmias. More specifically, the present invention provides for a system for developing a database of body surface ECG P wave data maps for classification and localization of left-sided atrial arrhythmias.

In accordance with exemplary embodiments of the present invention the method generally comprises receiving P wave data from two or more subjects; computing maps of the P wave data; classifying the maps and thereby creating classified maps; verifying the classified maps; averaging the classified and verified maps and thereby creating mean maps; and storing and accessing the mean maps in the database.

The P wave data may generally be obtained in a subject by electrically stimulating or pacing the left atrium using a probe by for example a retrograde aortic or a transseptal procedure. Alternatively, the P wave data may also be obtained during a spontaneously occurring or induced left atrial arrhythmia.

The maps may be computed from the P wave data in the form of P wave potential maps or P wave integral maps. The maps are classified based on spatial pattern characteristics.

The maps may be verified before averaging. The mean maps may then be calculated from the verified maps to construct a database of characteristic body surface ECG mean P wave maps specific to the origin of left atrial pacing or left atrial arrhythmia. The mean maps of the P wave data in the database can be used to automatically classify and localize P wave data from a patient obtained from a left atrial arrhythmia. For instance, P wave data can be obtained from an atrial tachycardia whereby the origin is localized, a focal atrial fibrillation whereby the origin of a single atrial premature beat or an initiating beat is localized, or an orthodromic AV reentrant tachycardia involving an accessory pathway whereby the atrial insertion of an accessory pathway is localized.

BRIEF DESCRIPTION OF THE FIGURES

The objectives and advantages of the present invention will be understood by reading the following detailed description in conjunction with the drawings, in which.

DETAILED DESCRIPTION

Figure 1:
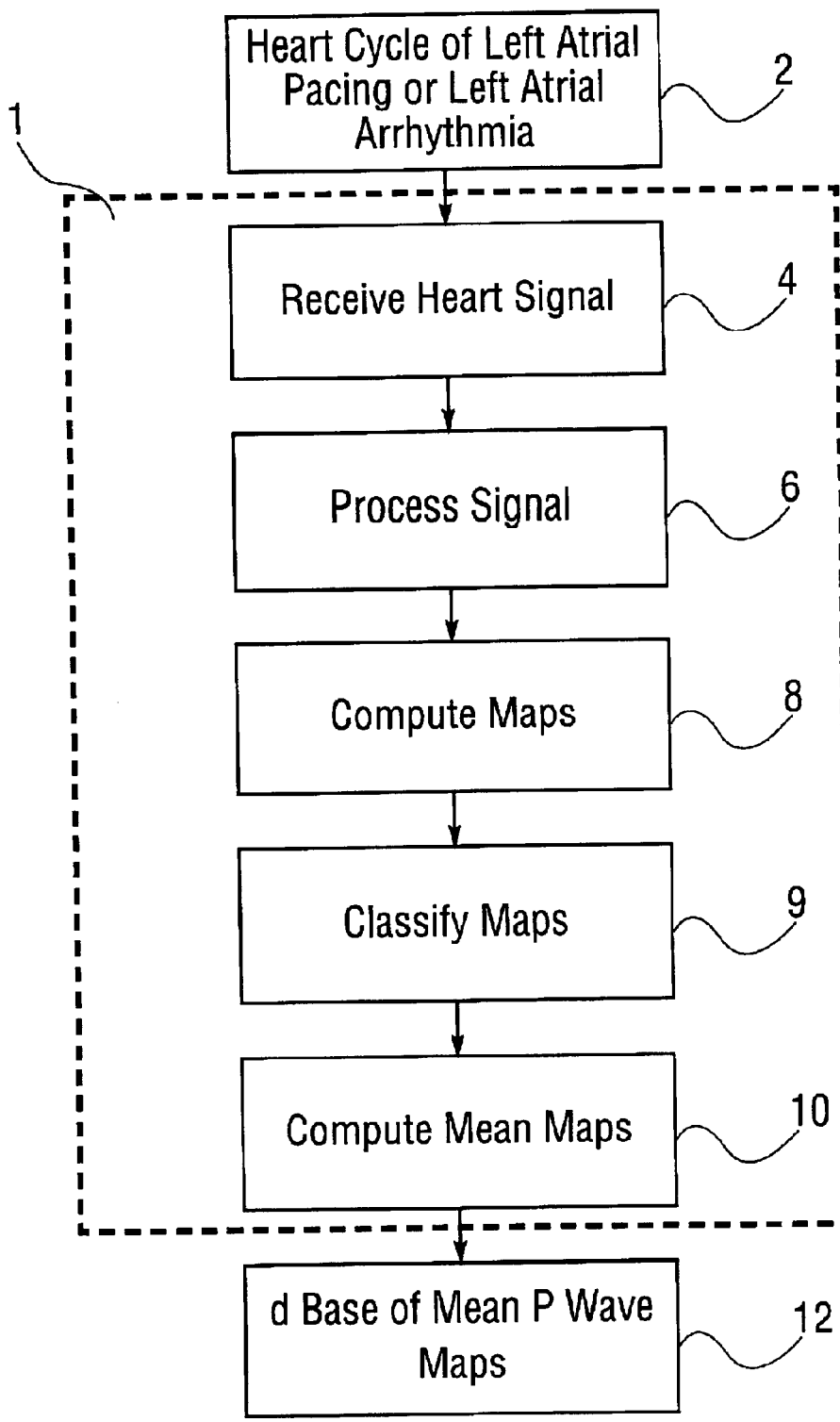
FIG. 1 depicts an overview of the development of a database of mean body surface ECG P wave data maps for classification and localization of left atrial arrhythmias according to an embodiment of the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention involves a system for developing a database of body surface ECG P wave data maps which allows a more intuitive and direct interpretation of the heart signals in terms of the underlying cardiac source. This database enables detailed noninvasive localization of left atrial arrhythmias by correlating subtle spatial differences in P wave morphology with various locations of ectopic atrial activity. The database is derived from P wave data of two or more subjects but can after its development be updated using additional and/or future P wave data of subjects to improve its resolution for discriminating focal atrial activity.

Clinical application of the database of P wave data maps enables improved noninvasive localization of left atrial arrhythmias prior to radiofrequency catheter ablation. Noninvasive localization of left atrial arrhythmias is important since it can target and minimize invasive catheter mapping to a small confined segment of the left atrium prior to ablation therapy delivery. Consequently, shorter and more efficient mapping and ablation procedures will result in less fluoroscopic exposure of the patient and physician as well as the patient will undergo less trauma and benefit from reduction in the procedure-related risk for clot formation and stroke. The database of the present invention can also be applied to noninvasively screen patients and localize arrhythmias before admitting a patient to the electrophysiology laboratory to undergo ablation therapy. This noninvasive screening and arrhythmia localization can easily be performed in an outpatient clinic or physician's office and enables improved decision making regarding the optimal choice of therapy, e.g. anti-arrhythmic drugs, permanent pacing, or ablation treatment, or combinations of these treatment modalities. Additionally, the database of the present invention also enables noninvasive follow-up of a patient to assess arrhythmia recurrences due to failure or disease progression after therapy delivery has taken place.

The embodiments of this invention relate to developing a database of mean multi-lead body surface P wave data map patterns that can be used to classify and localize left atrial arrhythmias. Examples of currently known left atrial arrhythmias are atrial tachycardia, focal atrial fibrillation, and orthodromic AV reentrant tachycardia involving an accessory pathway. The present invention may also be applied to other types of left atrial arrhythmias.

The use of body surface mapping allows ECG data presentation in a unique spatial format that contains a display of the P wave distribution on the entire torso surface. This electrocardiographic display format provides a better way to identify the focal source or reentrant circuit of atrial tachycardia, the focal source of atrial fibrillation, as well as the atrial insertion site of an accessory pathway with orthodromic AV reentrant tachycardia.

The method of the present invention is shown in the simplified flow diagram of FIG. 1. The electrical signal from a heart cycle 2 is a spontaneously occurring or induced left atrial arrhythmia or it can be obtained using left atrial pacing. One or more heart cycles 2 can be obtained in two or more subjects. The heart signal is received 4 as unipolar or bipolar ECG signals simultaneously obtained from an array of multiple electrodes on predetermined torso sites. During signal processing 6, leads with inferior signal quality are rejected and baseline adjustment is performed by linear interpolation. A series of potential maps of the P wave cycle is computed at 2-ms intervals (other intervals can also be used). In a potential map, the signal sensed at a time instant by sensors placed on a patient's torso is plotted on a representation of the torso, e.g. as a contour map or color map. P wave onset and offset are determined, for instance, at the time instant when a peak reference voltage, e.g., 30 $\mu$V is reached and when the peak voltage drops below the reference voltage, respectively. Other criteria as well as an automated detection of P wave onset and offset can also be used. Subsequently, a body surface ECG P wave integral map is computed 8 over this selected time interval. In an integral map, the signal sensed by sensors is integrated over a selected time interval and the integral is plotted on a representation of the torso, e.g. as a contour map or color map. Qualitative data classification 9 is carried out by grouping maps based on pattern similarity. Other methods of data classification based on, e.g. pattern recognition algorithms, neural networks, statistical routines or anatomical location of the left atrial ectopic origin, can also be used. Mathematical analysis using correlation coefficients is then performed to verify the qualitative data classification procedure. Furthermore, mean maps are computed 10 of the classified maps. The mean maps (also called mean P wave maps) obtained during left atrial pacing or spontaneous or induced left atrial arrhythmias are stored in a database 12. This unique database will then contain mean body surface P wave data maps for comparison to patient's body surface ECG P wave data maps to improve classification and localization of left atrial arrhythmias. The maps in the database provide a useful reference for localizing P wave data from a patient with left atrial arrhythmias such as atrial tachycardia, focal atrial fibrillation, or orthodromic AV reentrant tachycardia using an accessory pathway. By comparing a patient's arrhythmia data to the maps in the database, a physician can provide a better diagnosis and make better decisions for a treatment regimen for an individual patient.

Figure 2:
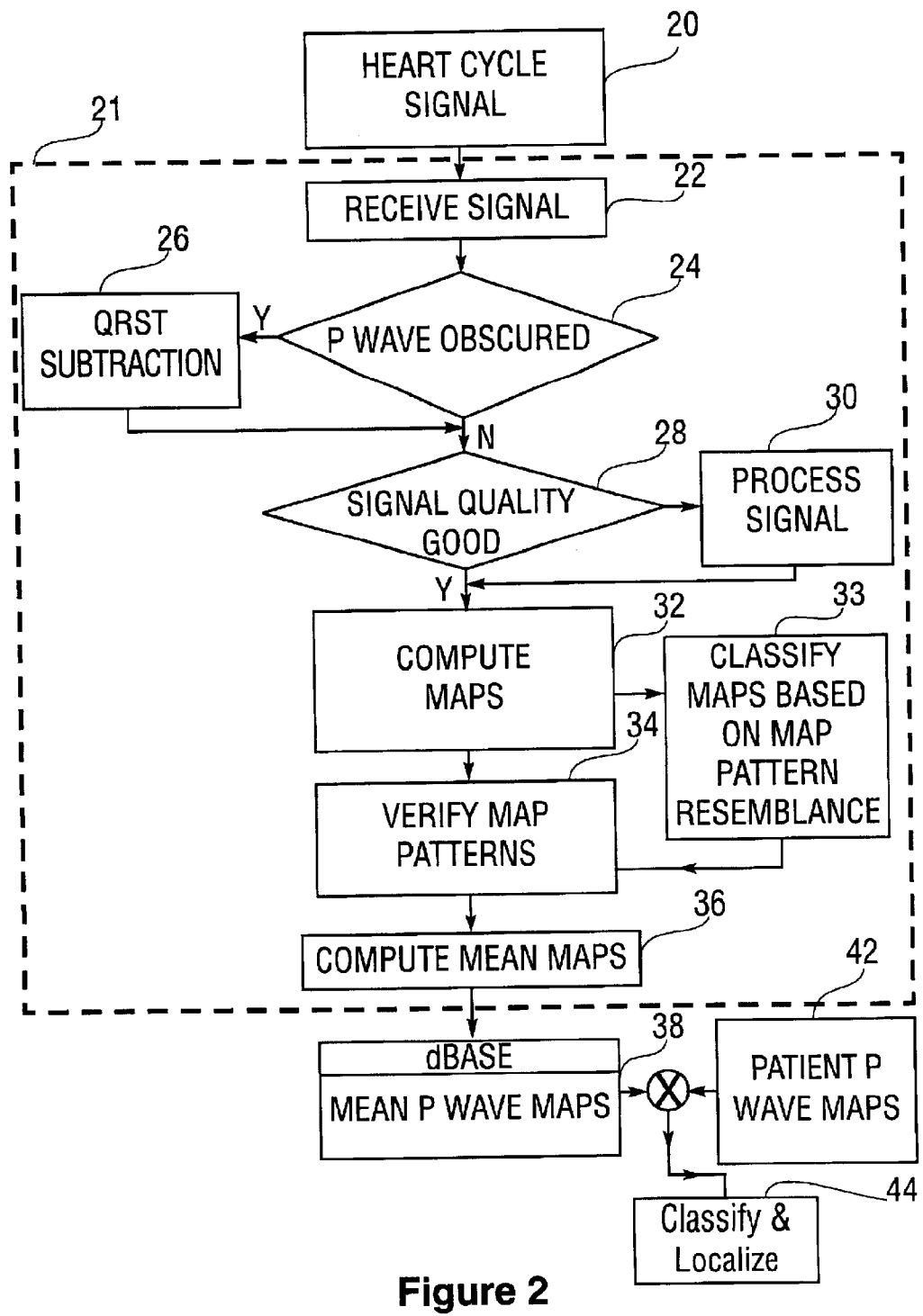
FIG. 2 depicts a system for developing a database of mean body surface ECG P wave data maps for classification and localization of left atrial arrhythmias to better classify and localize left atrial arrhythmias in patients according to an embodiment of the present invention.

Referring to FIG. 2, there is shown by means of a more detailed general flow diagram the overall sequence of steps to develop a database of body surface ECG P wave data maps for classification and localization of left atrial arrhythmias. One or more heart cycle signals 20 are acquired in two or more subjects. The electrical heart cycle signal 20 is obtained during left atrial pacing or spontaneously occurring left atrial arrhythmias. Left atrial pacing is performed using an electric stimulus probe such as a catheter using a transseptal or a retrograde aortic procedure. Alternative approaches or techniques other than a catheter are also feasible. Spontaneous left atrial arrhythmias can for example be atrial premature beats, atrial tachycardia, the initiating beat of focal atrial fibrillation, and the retrograde atrial activation during orthodromic AV reentrant tachycardia involving an accessory pathway. Left atrial arrhythmias can also be induced by programmed stimulation, pharmacologic challenge, or other means.

In a particular embodiment, left atrial pacing is conducted at 79 pacing sites (higher and lower numbers can also be used) under biplane fluoroscopic guidance in the 45 degree right and 45 degree left anterior oblique projections. Other fluoroscopic projections or other imaging techniques may also be used. A pacing protocol is aimed at accumulating pacing sites in key anatomical structures (i.e. pulmonary veins, around the circumference of the mitral annulus through the coronary sinus or directly from within the left atrium, the left atrial appendage, and the septum) as well as at obtaining additional coverage of the remainder of the left atrium. All pacing positions on the biplane fluoroscopic images are visually translated into positions on an anatomical diagram of the left atrium while the pacing protocol is in progress or immediately after its completion.

Figure 5A:
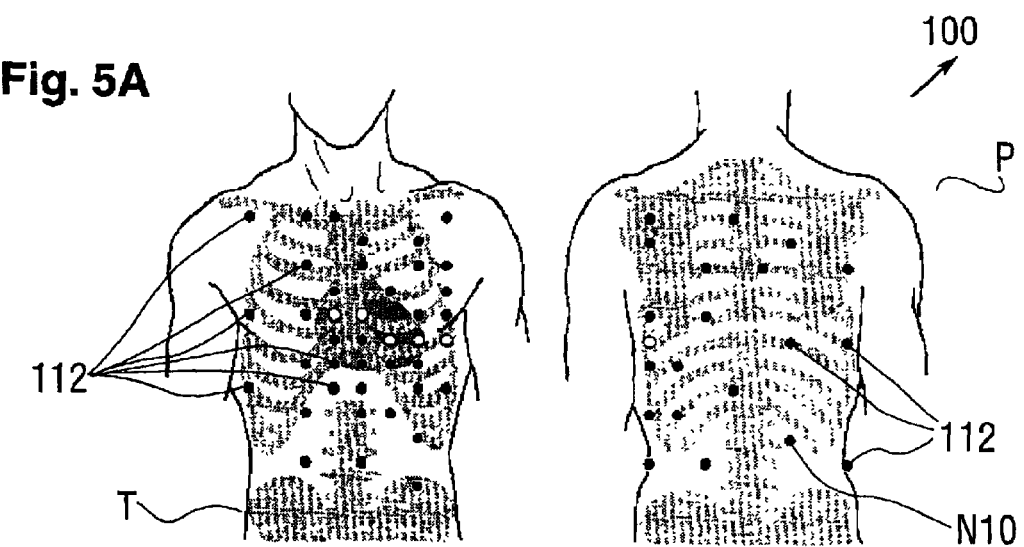
FIG. 5A depicts a sensor system having an array of sensing locations distributed across a subject's torso surface according to an embodiment of the present invention.

The heart cycle signal 20 is processed by a P wave classification routine 21. At step 22, the heart signal is received as unipolar or bipolar ECG signals simultaneously obtained from an electrode array on predetermined torso sites. Referring to FIG. 5A, the techniques of the present invention will generally make use of an array 100 of sensors 112 distributed across anterior and posterior skin surfaces of torso T on patient P. Array 100 provides multi-lead ECG data at a plurality of sensing locations distributed across the torso T, typically at over 20 sensing locations, more preferably at over 40 sensing locations, and ideally at 62 or more sensing locations.

Sensors 112 generally comprise unipolar or bipolar electrodes coupled to the patient's skin, or to an alternative accessible body surface (for example via a transesophageal approach) suitable for measuring electrical body surface potential. Suitable electrode structures may include those described in U.S. Pat. Nos. 5,311,873 and 5,634,469, which are incorporated herein by reference. Alternative sensor array structures and associated data acquisition and manipulation components may also be used.

ECG data is preferably acquired simultaneously from each of sensors 112 of array 100 at a sampling rate of over about 500 Hz, ideally at a sampling rate of about 1,000 Hz or more. In some embodiments, sequential sampling of sensors 112 from array 100 may alternatively be used, and higher or lower sampling rates also are feasible. When a lower sampling rate is used, the data may be upsampled using multirate filter banks.

Referring to FIG. 2, at step 24, if the P wave is obscured, e.g., due to the P wave activity coinciding with ventricular recovery of the preceding cardiac cycle, the QRST subtraction 26 routine can be invoked to separate the signals. It may be possible in some circumstances to artificially separate the P wave from the QRST interval, i.e., by the use of pharmacological compounds that temporarily block AV conduction or by electrical pacing of the ventricle. Alternatively, other signal separation methods and systems may also be used.

Figure 3:
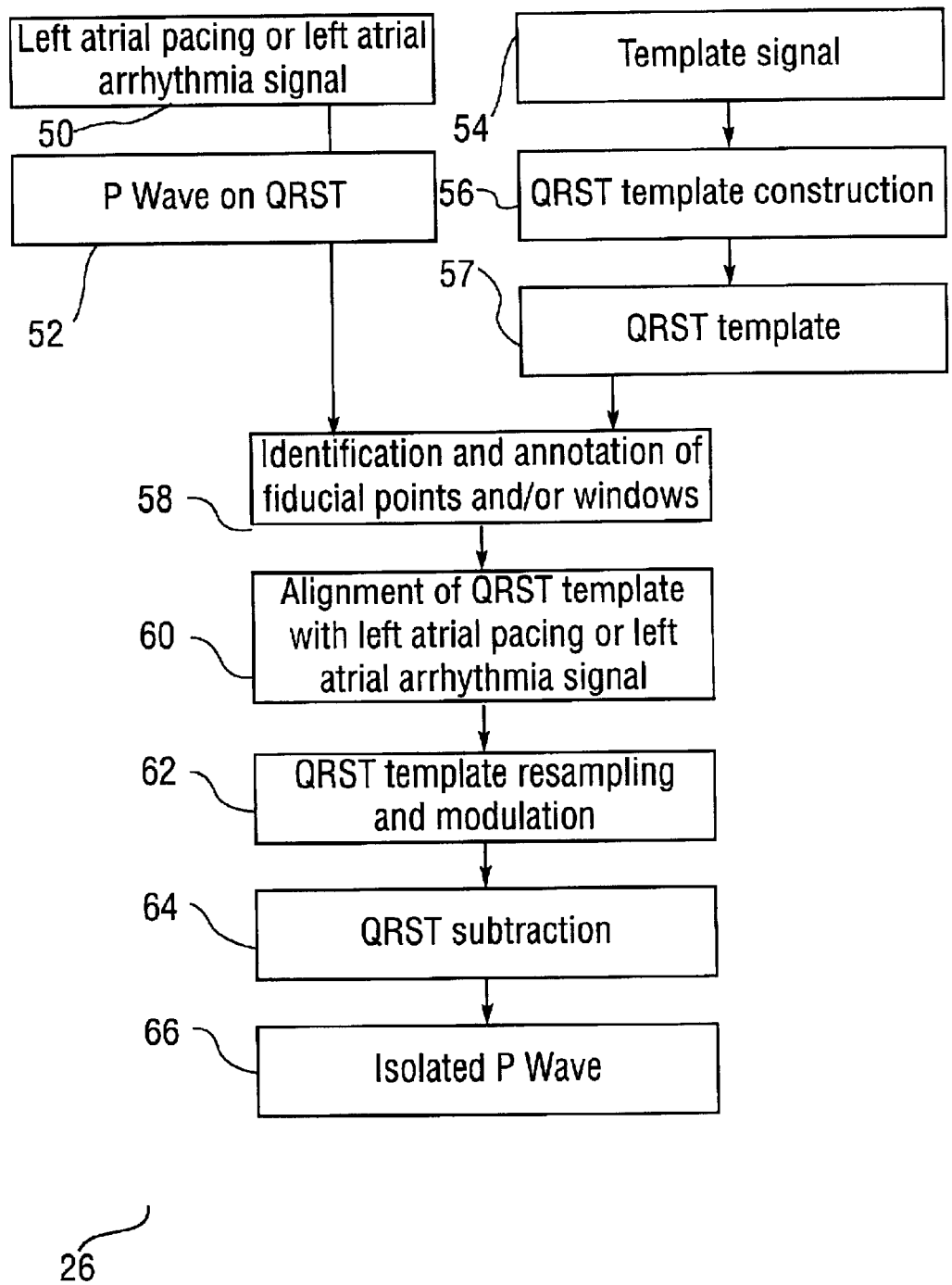
FIG. 3 depicts a method for separating obscured P waves from a superimposed QRST complex according to an embodiment of the present invention.

Referring to FIG. 3, the QRST subtraction routine 26 uses an adaptive QRST template constructed from averaged QRST complexes obtained from body surface ECG measurements to enable isolation of the otherwise obscured P wave activity.

The method of 26 generally includes recording of unipolar or bipolar ECG data from the array of torso sites in steps 50 and 54. The signal 50 is obtained during left atrial pacing or during a spontaneous or induced left atrial arrhythmia that contains electrical heart signals in which atrial activity is obscured by ventricular activity. This recorded signal 50 will also include both the P wave and a superimposed QRST signal portion 52 and is further referred to as the obscured P wave signal. The method 26 also receives at least two template signals 54 that contain electrical heart signals obtained during normal sinus rhythm or atrial overdrive pacing for the construction 56 of a QRST template 57. In the exemplary embodiment, about 100 cardiac cycles of 62-channel unipolar ECG data are recorded, although fewer cycles may be used if the spatial and temporal variations of the QRST complex are relatively low. Typically, more than ten cycles will be used, often more than 50 cycles for construction 56 of the QRST template 57.

An adaptation of the QT interval of the QRST template can take place to correct for differences in heart rate with the obscured P wave signal. One or more fiducial points and windows are identified and annotated 58 for both the QRST template to create a so called annotated QRST template as well as for the obscured P wave signal, to create a so called annotated obscured P wave signal. Alignment 60 of the one or more fiducial points and windows annotated in the annotated QRST template and the annotated obscured P wave signal then takes place. After the alignment 60 of the annotated QRST template and annotated obscured P wave signal, the annotated QRST template is resampled and modulated 62 to further compensate for remaining discrepancies in duration and/or voltage. This creates a resampled and modulated QRST template. The atrial activity contained in the obscured P wave signal is isolated by subtracting 64 the resampled and modulated QRST template from the obscured P wave and thereby generating an isolated P wave 66. It is important to realize that the QRST template is adaptive to optimize the subtraction by first aligning the QRST template and then resampling and modulating the QRST template. The reason is to account for a discrepancy in heart rate and voltage amplitude of the QRST template with the TU complex of the obscured P wave signal. The method 26 includes a variety of techniques that can be used to modulate and resample the QRST template. Generally, this approach of modulation and resampling allows for the surface ECG measurements to retain their intricate spatial and temporal detail within the P wave morphology. The method 26 is capable of unmasking and preserving subtle electrical heart signal details of the relatively low-voltage P wave despite the obscuring superimposed relatively high-voltage QRST complex.

Further details of QRST subtraction method 26 are described in, and are incorporated herein by reference, U.S. patent applications Ser. Nos. 09/809,719 and 09/808,728, both filed Mar. 14, 2001.

Figure 4:
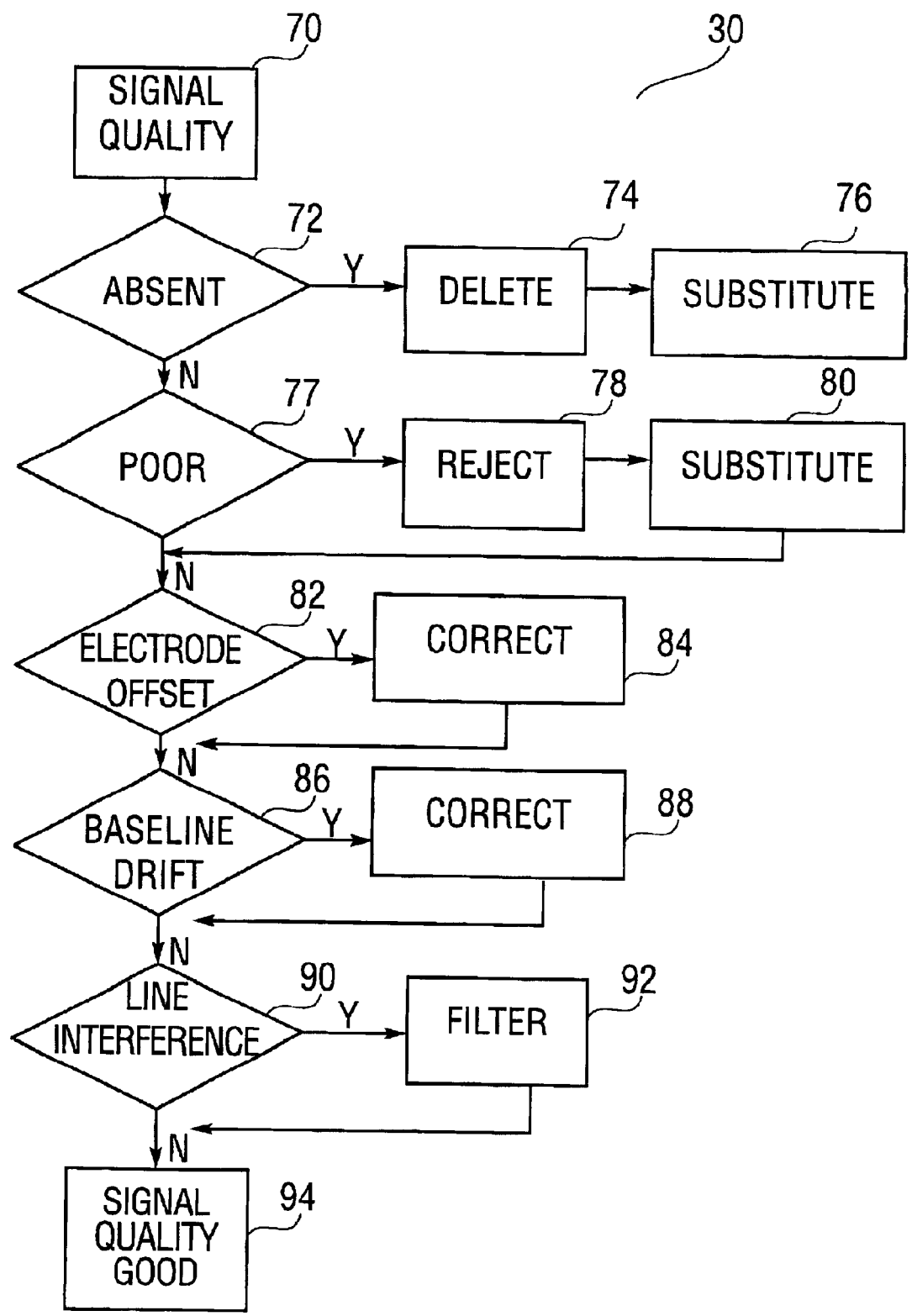
FIG. 4 depicts a method for selecting and processing good quality signals according to an embodiment of the present invention.

Referring to FIG. 2, all lead tracings are screened at step 28 in order to reject poor quality signals or signals from lead sites that are dislodged or obscured by defibrillation patches on the front and back of the subject's chest. The details of the signal-processing step 30 are depicted in the flow diagram of FIG. 4. All lead tracings are visually or automatically screened for signal quality 70. Absent signals 72 are detected and deleted 74, and substitute values 76 are interpolated based on adjoining lead recordings. Poor quality signals 77 are detected and rejected 78, and substitute values 80 are interpolated based on adjoining lead recordings. Interelectrode offset differences 82 are corrected 84 and linear baseline drift 86 is corrected 88. Both the offset and drift may be corrected 84, 88 by using linear interpolation after selecting one or more isoelectric time instants or intervals. Digital filtering to remove line frequency interference 90 is performed when necessary with a filter 92 such as a 60-Hz notch filter or other type of filter. Other means of filtering can also be used. The end result of the signal processing 30 is a good quality signal 94.

Figure 5B:
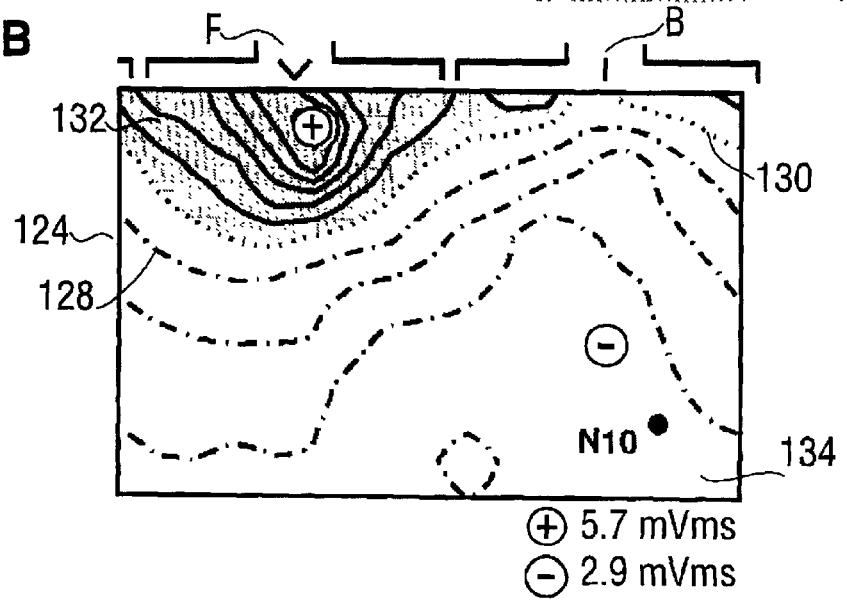
FIG. 5B depicts a body surface P wave integral map; a plot of a data matrix generated by mapping the integral values with positions corresponding to the location of the sensors across a subject's torso surface according to an embodiment of the present invention.
Figure 5C:
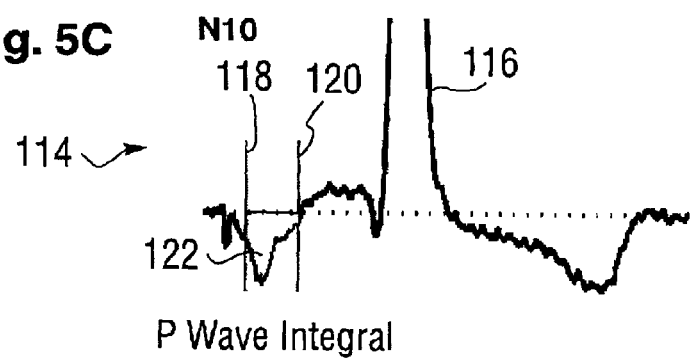
FIG. 5C depicts an ECG tracing illustrating a method for calculating an integral value across a selected time interval of a heart signal cycle from a single sensor location according to an embodiment of the present invention.

Referring to FIG. 2, by way of example, P wave integral maps are computed 32 as follows. Electrocardiographic data is analyzed by determining the onset and offset of the P wave. Subsequently, an integral map is computed over this selected time interval. Referring to FIG. 5C, graph 114 includes an ECG signal tracing 116 representing the variation in voltage over time. Signal tracing 116 may be used to evaluate heart cycle signals. In general, one or more reference heart cycles will be selected for manipulation and comparison. ECG tracing 116 can be used to determine an onset (starting time) 118 and offset (ending time) 120 of a time interval 122 of the heart signal cycle that is of interest for evaluating one or more regions of the heart. For instance, P wave onset and offset can be determined at the time instant when a peak reference voltage, e.g., 30 $\mu V$ is reached and when the peak voltage drops below the reference voltage, respectively. Alternative criteria for determining P wave onset and offset might also be used, and automated detection of time interval 122 is also feasible. Instead of a time interval, single or multiple time instants in the P wave cycle may also be selected.

FIG. 5A shows an exemplary map of sensor locations 112 on the front and back of a subject's torso. FIG. 5B shows an exemplary plot of a data matrix generated by mapping the integral values with positions corresponding to the location of the sensors 112 across a torso T of a patient P in FIG. 5A. FIG. 5C shows the calculation of an integral value from a plot 114 of heart cycle signal 116. In the exemplary embodiment of FIG. 5C, a P wave integral numerical value may be calculated based on heart cycle signals 116 within selected time interval 122 having an onset 118 and an offset 120 for a particular sensor location N10. This calculated P wave integral value reflects the time/amplitude area of ECG signal at the sensor location within the selected time interval. Similar integral values are calculated for each sensor location, and the sensor values are mapped within data matrix 124 continuously from a portion of the data matrix associated with a front F of torso T, across a side of the patient P, and to a back B portion of torso T. As shown in FIG. 5B, the data matrix will often be presented graphically by calculating and plotting lines of constant integral values 128 based on the individual discrete integral values and their associated positions within the data matrix. In some embodiments, this information can be summarized by presenting a single line 130 of zero integral value between a region of positive integral values 132 and a region of negative integral values 134. Alternatively, 3-D or chest anatomy-based representations of the data matrix and/or color plots may be used to represent the data matrix wherein different colors represent different integral values or ranges of integral values. Of course, contour maps or color plots of potential values that represent P wave data may also be plotted as set forth above.

Referring again to FIG. 2, the P wave data maps are classified visually at step 33 according to a correspondence in the spatial location and mutual orientation of its map extremes and zero line configuration. This will result in one or more groups of P wave data maps with nearly identical P wave morphology. Alternative methods to classify and group the P wave data maps, e.g. pattern recognition algorithms, neural networks, statistical analysis or an anatomical subdivision of the location of the left atrial ectopic origin, may also be used. At step 34, quantitative data verification is carried out by subjecting the groups of P wave data maps to a mathematical analysis using correlation coefficients in order to compare the uniformity of the P wave pattern within each group and the variability of the P wave pattern between groups. Other methods of quantitative data evaluation, statistical or the like, may also be used.

Figure 6:
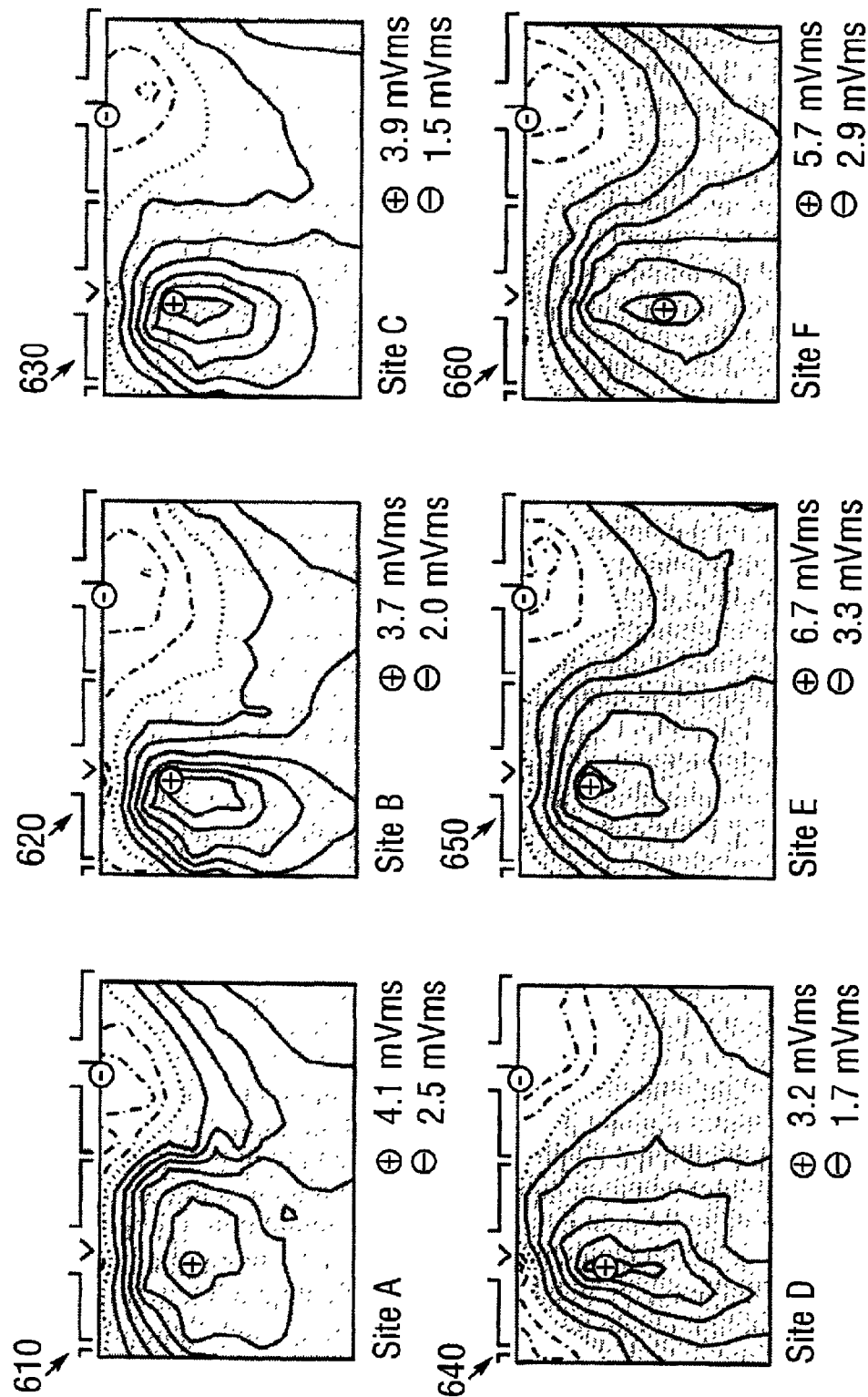
FIG. 6 depicts six mean body surface P wave integral maps obtained during pacing at the left upper or left lower pulmonary vein according to an embodiment of the present invention.

Mean maps are then computed at step 36 to form for instance mean P wave integral maps from a group of nearly identical P wave integral maps obtained in different patients. FIG. 6, depicts a group of nearly identical P wave body surface integral maps obtained during pacing at the left upper (site A 610, B 620, D 640, E 650 and F 660) and left lower pulmonary vein (site C 630). The displayed map patterns are all spatially compatible with regard to the location and orientation of the extremes and zero line contour.

Referring again to FIG. 2, the mean P wave data maps are stored in reference database 38. Database 38 contains mean P wave maps of a variety of ectopic origins in the left atrium. The ectopic origin of each mean map is determined for left atrial pacing as well as for spontaneously occurring or induced left atrial arrhythmias. In case of left atrial pacing, biplane fluoroscopy or other imaging modality is used, such as e.g. ultrasound, to determine the anatomical location of the pacing that was performed with a probe or catheter. In case of spontaneously occurring left atrial arrhythmias, similar imaging techniques can be used, while multipolar catheter electrogram recordings or alternative methods are used to determine the origin of the arrhythmias.

P wave body surface ECG integral maps of a given patient's left atrial arrhythmia 42 can subsequently be compared at step 44 to the reference database 38 to classify and localize the origin of that patient's left atrial arrhythmia. Consequently, a unique database is available for improved classification and localization of left atrial arrhythmias. The resolution of the database can always be updated and improved by adding new and/or more detailed information related to the P wave data and the underlying ectopic origin sites.

Figure 7A:
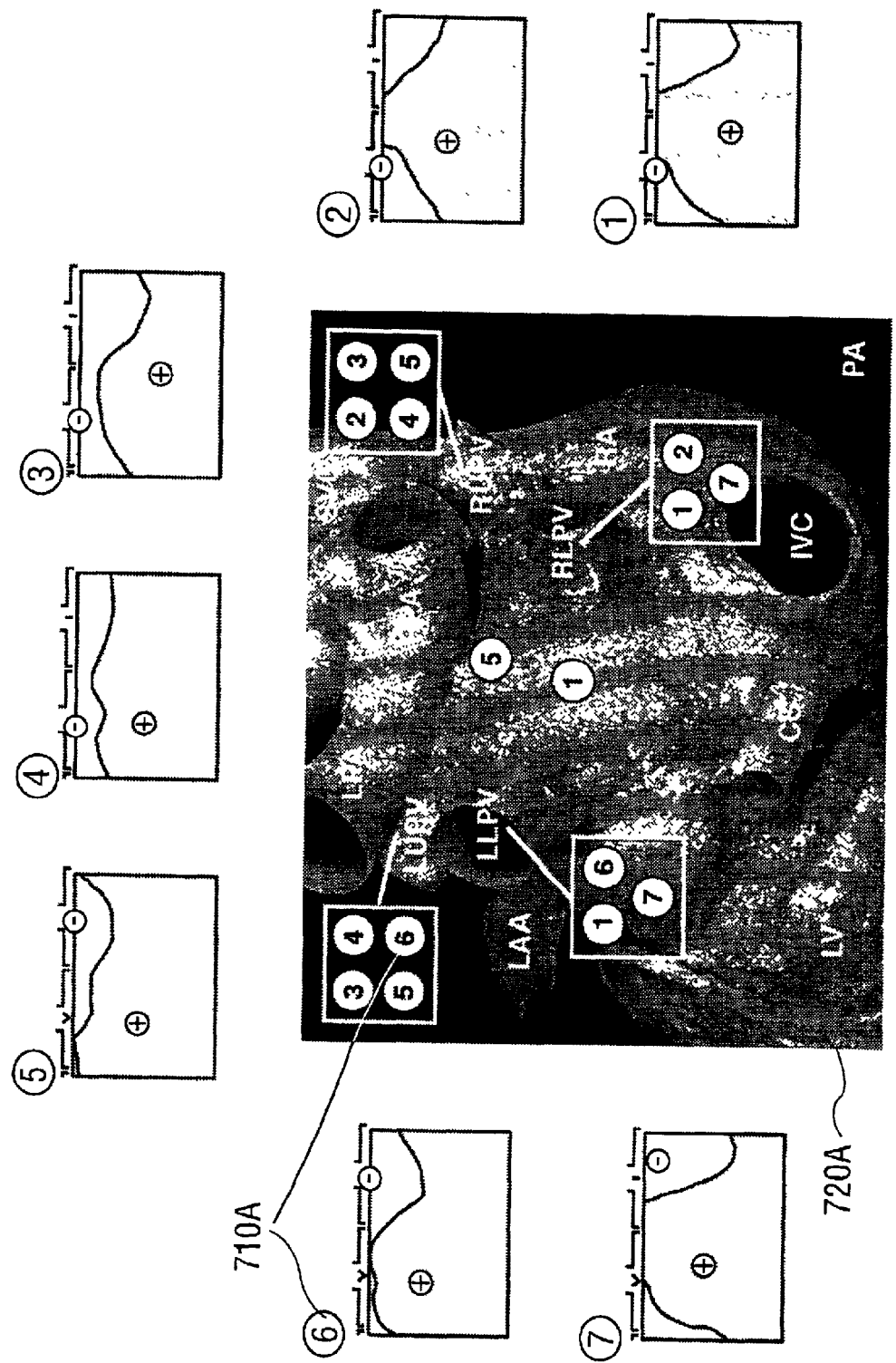
FIG. 7A depicts different mean P wave integral maps and their associated segments of pacing origin represented in a postero-anterior view of the left atrium according to an embodiment of the present invention.
Figure 7B:
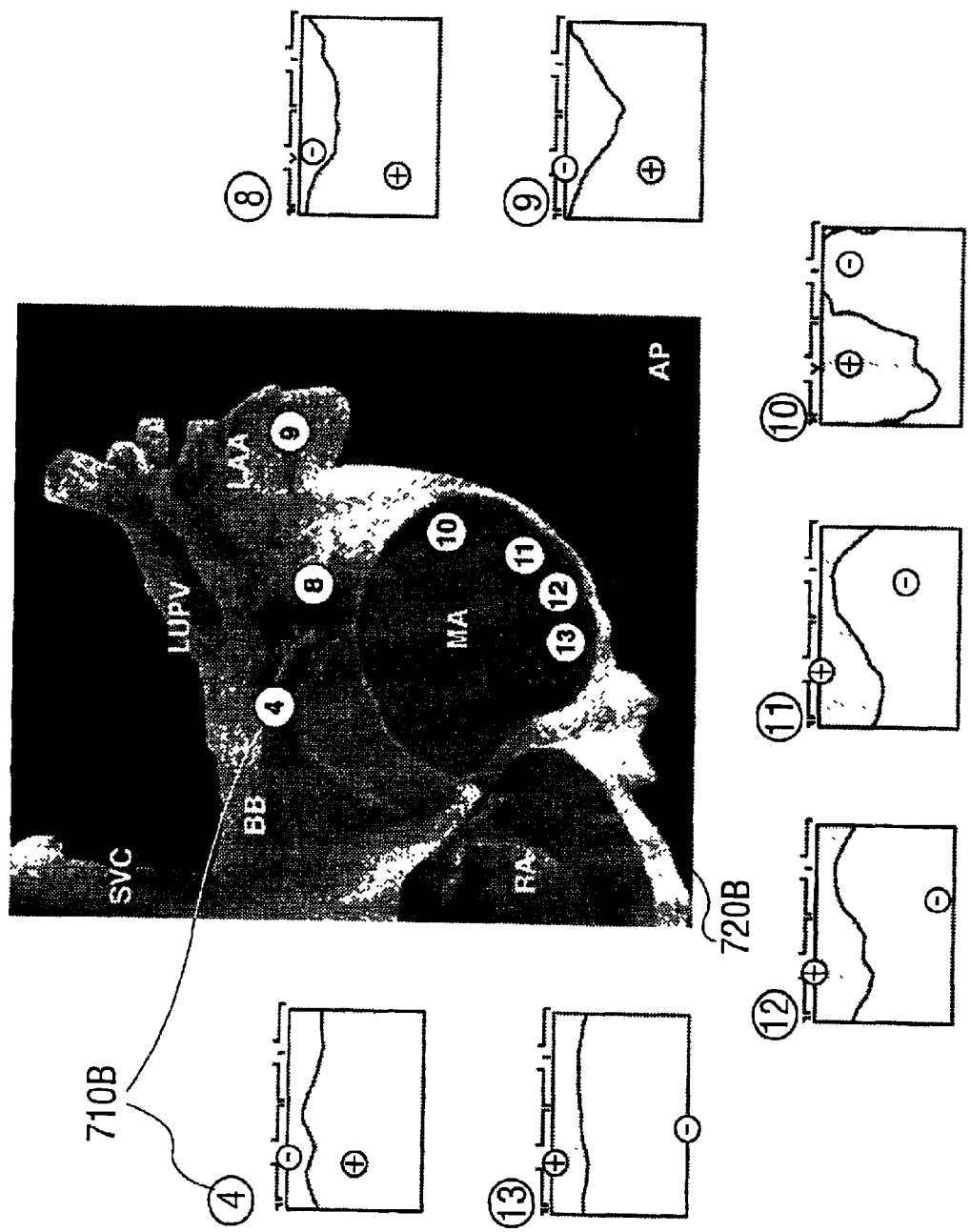
FIG. 7B depicts different mean P wave integral maps and their associated segments of pacing origin represented in an antero-posterior view of the left atrium according to an embodiment of the present invention.
Figure 7C:
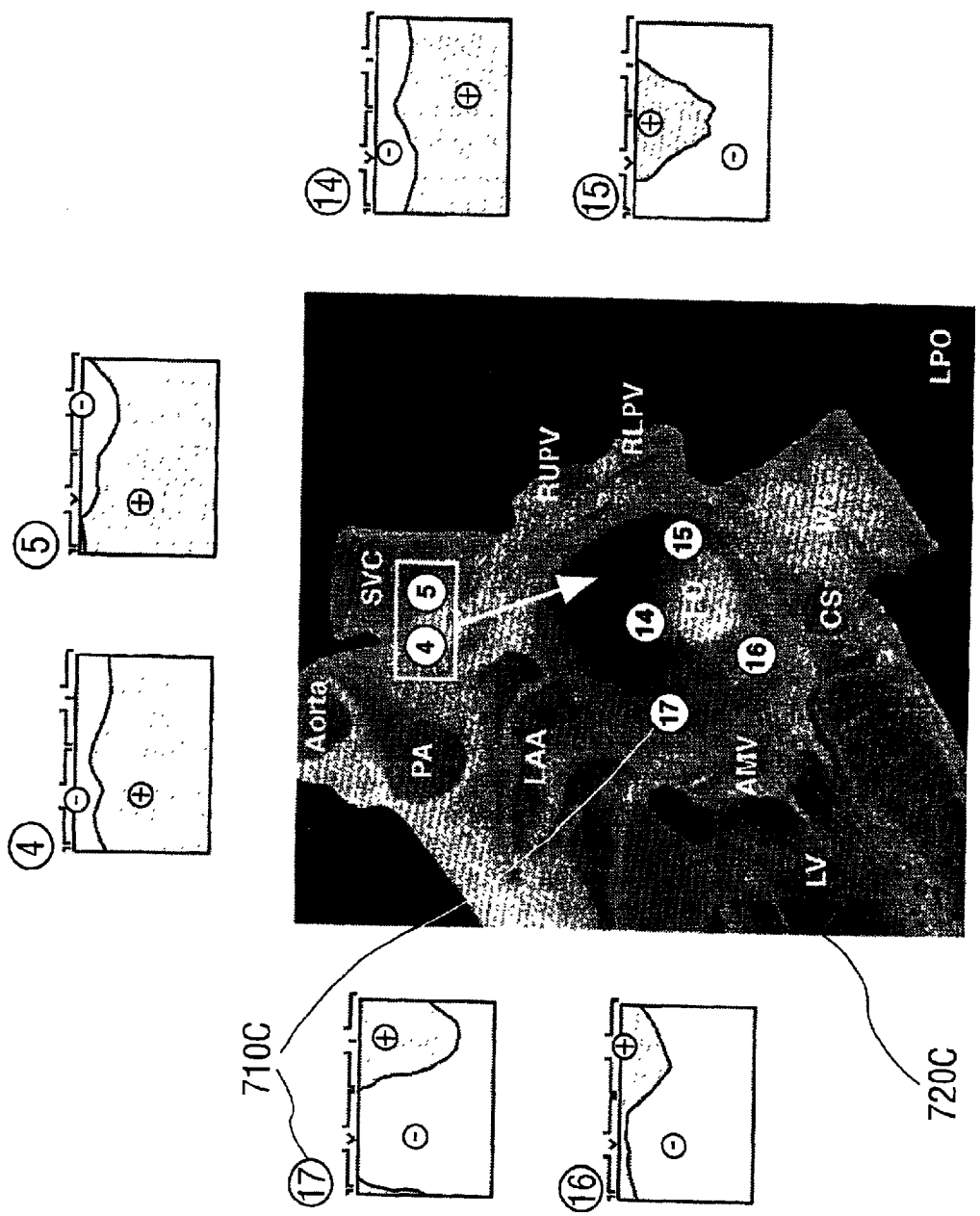
FIG. 7C depicts different mean P wave integral maps and their associated segments of pacing origin represented in a left posterior oblique view of the left atrium according to an embodiment of the present invention.

Referring to FIGS. 7A, 7B, 7C, databases of 17 different mean P wave integral map patterns are generated by left atrial pacing according to an embodiment of the present invention. Higher or lower number for the groups with nearly identical P wave morphology can also be used. A higher number of groups improves the resolution of the database and thereby of the classification and localization of the left atrial arrhythmias. The encircled numbers 710A, 710B, and 710C relate maps to a specific endocardial segment of pacing origin shown in the anatomical diagrams 720A, 720B and 720C. Endocardial segments of pacing can also be delineated as single points, clusters of points, or the like. Other anatomical or schematic diagrams of the left atrium can also be used. Representation of the endocardial segments of pacing may also include biplane fluoroscopic views. The mean P wave integral map display features extreme positions and zero line contour without positive and negative contour lines. Different forms of map format (e.g. 3-D or chest anatomy-based format) or map display (e.g. use of various color schemes) can also be used. The three dimensional diagrams offer a postero-anterior (PA, 720A in FIG. 7A), an anteroposterior (AP, 720B in FIG. 7B), and a left posterior oblique view (LPO, 720C in FIG. 7C) of the left atrium. Major anatomical landmarks are highlighted: the left (LPA) and right (RPA) pulmonary artery; the superior (SVC) and inferior (IVC) vena cava; the left atrial appendage (LAA); right atrium (RA); coronary sinus (CS); the left ventricle (LV); the left upper (LUPV), left lower (LLPV), right upper (RUPV), and right lower (RLPV) pulmonary vein; Bachmann's bundle (BB); mitral annalus (MA); anterior mitral valve leaflet (AMV); and the fossa ovalis (FO).

Figure 8:
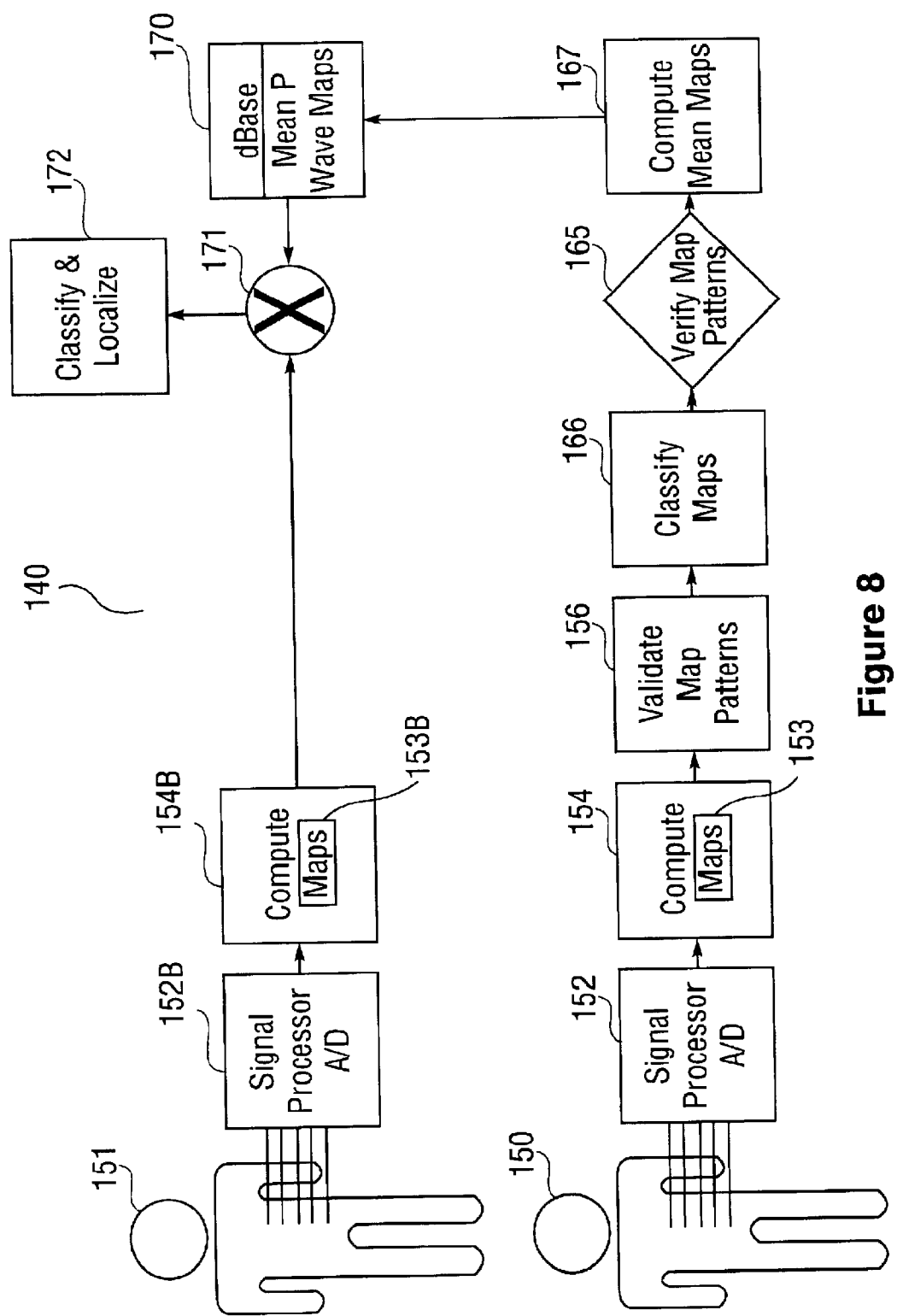
FIG. 8 depicts the design of an apparatus for classifying and localizing left-sided atrial arrhythmias according to an embodiment of the present invention.

Referring to FIG. 8, the design of an apparatus 140 for classifying and localizing left atrial arrhythmias is described. The apparatus 140 obtains data for development of a database by recording unipolar or bipolar ECG tracings from a plurality of predetermined torso sites on a subject 150. In a preferred embodiment, the tracings are obtained from an array of 62 unipolar electrodes during spontaneously occurring or induced left atrial arrhythmia or left atrial pacing. Alternatively, a smaller or larger number of electrodes or a different distribution of electrodes on the torso can also be used.

Electrocardiographic data from the electrodes are received by a signal processor 152. The electrocardiographic data may be acquired simultaneously by the signal processor 152 at a 1000 Hz sampling rate using a multi-lead ECG recording system. Alternatively, the signal processor can perform sequential sampling. Other data rates may also be used. The data can be upsampled using multirate filter banks when a lower sampling rate is used. The signal processor 152 may delete absent signals due to electrode obscurement by defibrillator patches or lead dislodgment. The signal processor 152 may automatically identify and reject poor quality signals. Alternatively, poor quality signals may be visually identified and rejected. These rejected signals may be substituted by interpolating adjacent lead recordings. The signal processor may also correct for interelectrode offset differences and linear baseline drift, e.g., using linear interpolation after selecting one or more isoelectric time instants or intervals (other techniques for baseline adjustment can also be used). The signal processor 152 may incorporate digital filtering to remove line frequency interference when necessary, e.g., with a 60-Hz notch filter (other types of filter or means of filtering may also be used).

A computing means 154 coupled to the signal processor 152 computes one or more maps 153, e.g., potential maps, of the P wave, e.g., at 2-ms intervals (other intervals can also be used). The potential maps are visually evaluated to determine P wave onset and offset as the point in time when one of the extreme values supersedes and returns within a 30 $\mu V$ reference voltage window around the zero line. Alternatively, other criteria for P wave onset and offset can also be used as well as the onset and offset can be automatically detected. In a particular embodiment, an integral map 153 of the selected time interval in the P wave cycle is computed. As an alternative, the computing means 154 may compute P wave potential maps at single or multiple selected time instants. The computing means 154 may include software or hardware or some combination of both. Furthermore, the computing means may be incorporated into signal processor 152.

A validating means 156 then validates the patterns in the maps 153. The validating means typically includes circuitry or software for waveform analysis or filtering to determine if a given map pattern makes sense. For example, the validating means may reject any map for which the integral or potential values lie outside of a predetermined range. Alternatively, the validating means 156 may display the map for visual inspection by an expert.

A classifying means 166 classifies one or more groups of P wave data maps with nearly identical P wave morphology. Alternative methods to classify and group the P wave data maps, e.g. pattern recognition algorithms, neural networks, statistical analysis or an anatomical subdivision of the location of the left atrial ectopic origin, may also be used. Once the maps 153 have been classified in groups based on pattern resemblance, a verifying means 165 will mathematically evaluate group selection using correlation coefficients to compare intragroup pattern uniformity and intergroup pattern variability. The verifying means 165 may also perform statistical analysis on the map patterns in the groups 153, e.g. to determine if the map patterns lie within a statistical margin for error. Subsequently, an averaging means 167 averages the classified maps that lie in the same classification. The mean maps are then stored in the reference database 170. Classified map patterns from a plurality of subjects 150 build up the database 170. Once the database contains a sufficient number of mean map patterns, the apparatus 140 may be used to classify and localize 172 a left atrial arrhythmia in a patient 151 by comparing 171 P wave map patterns 153B from the patient with the mean P wave map patterns in the database 170. The P wave maps 153B (e.g. potential or integral maps) of patient 151 are obtained in a similar way as for the generation of the database 170 as shown in FIG. 8. This means that electrocardiographic data from the patient 151 is received by a signal processor 152B, and a computing means 154B to compute one or more maps 153B.

Figure 9:
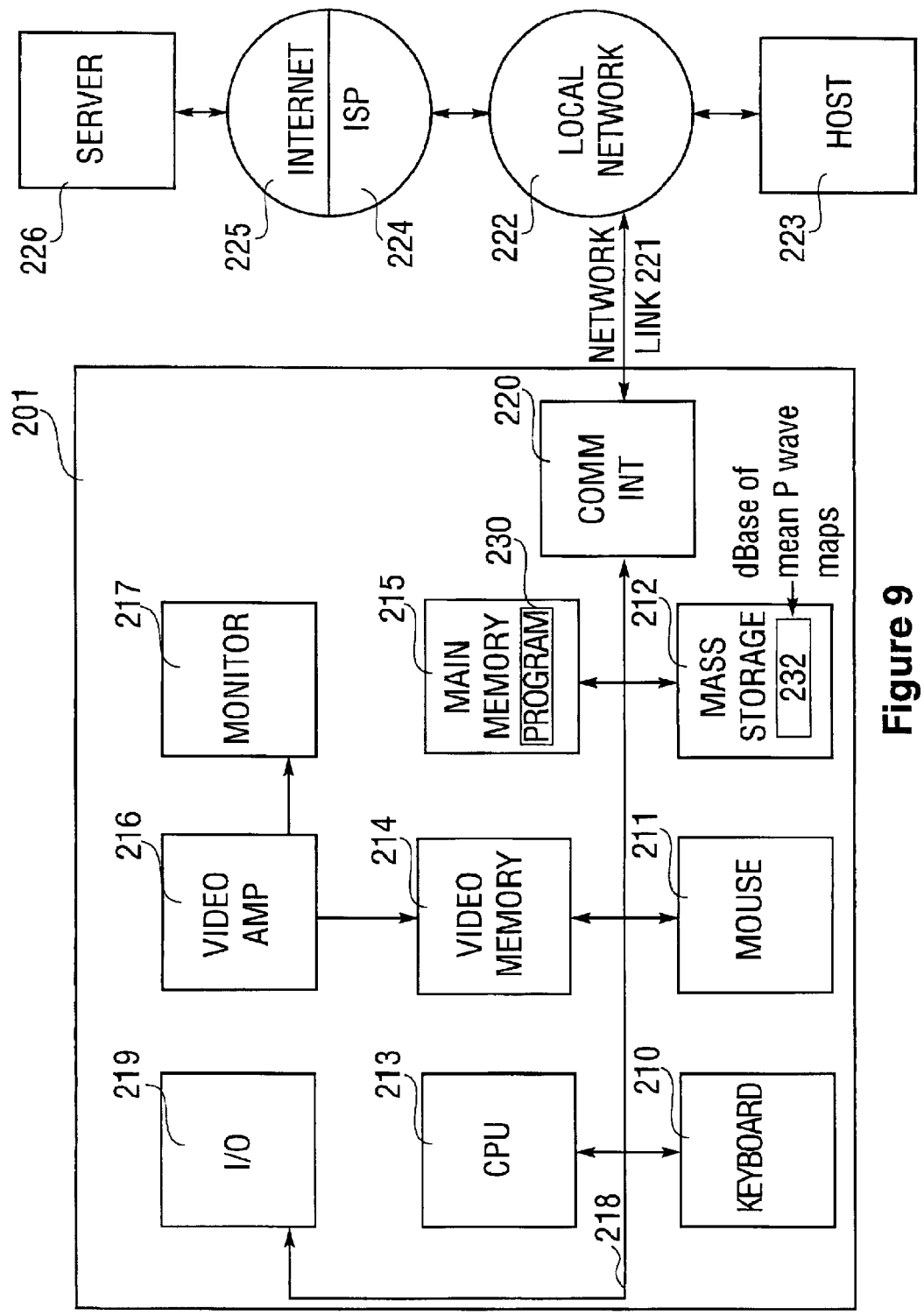
FIG. 9 depicts a block diagram of storing a database of mean body surface ECG P wave data maps in a computer-readable medium for retrieval, analysis and sharing according to an embodiment of the present invention.

Referring to FIG. 9, an embodiment of the invention can be implemented as computer software in the form of computer readable code executed on a general purpose computer such as computer 201, or in the form of bytecode class files running on such a computer. A keyboard 210 and a mouse 211 are coupled to a bi-directional system bus 218. The keyboard and mouse are for introducing user input to the computer system and communicating that user input to processor 213. Other suitable input devices may be used in addition to, or in place of, the mouse 211 and keyboard 210. I/O (input/output) unit 219 coupled to bi-directional system bus 218 represents such I/O elements as a printer, A/V (audio/video), I/O, etc. Computer 201 includes a video memory 214, main memory 215 and mass storage 212 (database storage), all coupled to bi-directional system bus 218 along with keyboard 210, mouse 211 and processor 213. The mass storage 212 may include both fixed and removable media, such as magnetic, optical or magnetic optical storage systems or any other available mass storage technology. Bus 218 may contain, for example, thirty-two address lines for addressing video memory 214 or main memory 215. The system bus 218 also includes, for example, a 32-bit data bus for transferring data between and among the components, such as processor 213, main memory 215, video memory 214 and mass storage 212. Alternatively, multiplex data/address lines may be used instead of separate data and address lines.

In an embodiment of the invention, any suitable microprocessor or microcomputer may be utilized as processor 213. Main memory 215 may be a random access memory (RAM), dynamic random access memory (DRAM) or an equivalent. The main memory 215 typically contains a program 230 having instructions executable by the processor 213. In a preferred embodiment, the program 230 contains processor executable instructions that implement the steps of the method 1 of FIG. 1 or method 21 of FIG. 2. Alternatively, the program 230 may be stored wholly or partly in the mass storage 212. The mass storage 212 may contain database 232 of mean P wave maps for use with the program 230. The database may have features in common with the database 38 and 170 described above in relation to FIG. 2 and FIG. 8, respectively.

Video memory 214 may be a dual-ported video random access memory. One port of the video memory 214 is coupled to video amplifier 216. The video amplifier 216 is used to drive the display 217 (i.e. CRT, LCD). The video amplifier and the monitor may be implemented by any suitable apparatus.

Computer 201 may also include a communication interface 220 coupled to bus 218. Communication interface 220 provides a two-way data communication coupling via a network link 221 to a local network 222. For example, if communication interface 220 is an integrated services digital network (ISDN) card or a modem, communication interface 220 provides a data communication connection to the corresponding type of telephone line, which comprises part of network link 221. If communication interface 220 is a local area network (LAN) card, communication interface 220 provides a data communication connection via network link 221 to a compatible LAN. Wireless links are also possible. In any such implementation, communication interface 220 sends and receives electrical, electromagnetic or optical signals that carry digital data streams representing various types of information.

Network link 221 typically provides data communication through one or more networks to other data devices. For example, network link 221 may provide a connection through local network 222 to a local server computer or host 223 or to data equipment operated by an Internet Service Provider (ISP) 224. ISP 224 in turn provides data communication services through the world wide packet data communication network now commonly referred to as the "Internet" 225. Local network 222 and Internet 225 both use electrical, electromagnetic or optical signals that carry digital data streams. The signals through the various networks and the signals on network link 221 and through communication interface 220, which carry the digital data to and from computer 201, are exemplary forms of carrier waves transporting the information.

Computer 201 can send messages and receive data, including program code, through the network(s), network link 221, and communication interface 220. In the Internet example, remote server computer 226 might transmit a requested code for an application program or specific electrocardiography database through Internet 225, ISP 224, local network 222 and communication interface 220. Consequently, they provide an important link for rapid medical information exchange such as telemedicine.

The received code may be executed by processor 213 as it is received, and/or stored in mass storage 212, or other non-volatile storage for later execution. In this manner, computer 201 may obtain application code in the form of a carrier wave.

Application code (i.e. database, procedures, etc.) may be embodied in any form of computer program product. A computer program product comprises a medium configured to store or transport computer readable code, or in which computer readable code may be embedded. Some examples of computer program products are CD-ROM disks, ROM cards, floppy disks, magnetic tapes, computer hard drives, servers on a network, and carrier waves.

The computer systems described are for purposes of example only. An embodiment of the invention may be implemented in any type of computer system or programming or processing environment.

The ability to rapidly acquire, store, analyze and share medical information is necessary considering the rapid rate of change in medical technology. This computer 201 embodiment provides a database system capable of acquiring, analyzing, displaying and storing patient data in real time locally. In addition, communicating with other medical research centers allows sharing of medical information which can add new techniques and enlarge the subject database by the addition of new data elements from other centers.

It will be clear to one skilled in the art that the above embodiment may be altered in many ways without departing from the scope of the invention. Accordingly, the scope of the invention should be determined by the following claims and their legal equivalents.

What is claimed is:

1. A system for developing a database of body surface ECG P wave data for classification and localization of left atrial arrhythmias wherein said database is derived from P wave data of two or more subjects comprising:

(a) means for receiving said P wave data from a subject;

(b) means for classifying said P wave data and thereby creating classified P wave data;

(c) means for averaging said classified P wave data and thereby creating mean P wave data; and (d) means for storing and accessing said mean P wave data in said database.

2. The system as set forth in claim 1, wherein one of said left atrial arrhythmias is an atrial tachycardia, a focal atrial fibrillation, or an orthodromic AV reentrant tachycardia involving an accessory pathway.

3. The system as set forth in claim 1, wherein said P wave data is in the form of maps.

4. The system as set forth in claim 3, wherein said maps are in the form of integral maps.

5. The system as set forth in claim 3, wherein said maps are in the form of potential maps.

6. The system as set forth in claim 1, further comprises means for obtaining said P wave data by electrically stimulating a left atrium of said subject using a probe.

7. The system as set forth in claim 6, wherein said P wave data is obtained using a transseptal procedure.

8. The system as set forth in claim 6, wherein said P wave data is obtained using a retrograde aortic procedure.

9. The system as set forth in claim 1, further comprises means for obtaining said P wave data from spontaneously occurring left atrial arrhythmias.

10. The system as set forth in claim 1, further comprises means for obtaining said P wave data by inducing left atrial arrhythmias.

11. The system as set forth in claim 1, wherein said receiving means further comprises means for sensing heart cycle signals while said subject is spontaneously producing a left atrial arrhythmia, while a left atrial arrhythmia is induced in said subject, or while a left atrial pacing is being performed in said subject.

12. The system as set forth in claim 11, wherein said receiving means further comprises means for detecting an electrical heart signal with a plurality of sensors proximate a subject's torso.

13. The system as set forth in claim 12, wherein said receiving means further comprises means for separating from said electrical heart signal an atrial signal obscured by a ventricular signal.

14. The system as set forth in claim 12, wherein said receiving means further comprises means for selecting at least one reference cycle from among a plurality of heart cycles to determine said P wave data.

15. The system as set forth in claim 14, wherein said receiving means further comprises means for selecting a time interval of said reference cycle and comparing signals from said plurality of sensors during said selected time interval.

16. The system as set forth in claim 15, wherein said receiving means further comprises means for generating a data matrix by integrating said signals from each sensor location within said selected time interval to define an integral value, and arranging said integral value within said matrix according to locations of said associated sensor locations along a surface of said subject's torso.

17. The system as set forth in claim 16, wherein said receiving means further comprises means for computing an integral map over said selected time interval and plotting said data matrix.

18. The system as set forth in claim 17, wherein said computing means further comprises means for determining lines of constant integral values, and identifying maps of said P wave data using said lines of constant integral values mapped upon representations of said surface of said subject's torso.

19. The system as set forth in claim 17, wherein said computing means further comprises means for representing different integral values by one or more different colors mapped upon representations of said surface of said subject's torso.

20. The system set forth in claim 15, wherein said receiving means further comprises means for generating a data matrix of potential signals from each sensor location within said selected time interval to define one or more potential values, and arranging said potential values within said matrix according to locations of said associated sensor locations along said surface of a subject's torso.

21. The system set forth in claim 20, wherein said receiving means further comprises means for computing one or more potential maps over said selected time interval and plotting said data matrix.

22. The system as set forth in claim 21, wherein said computing means further comprises means for determining lines of constant potential values, and identifying maps of said P wave data using said lines of constant potential values mapped upon representations of said surface of said subject's torso.

23. The system as set forth in claim 21, wherein said computing means further comprises means for representing different potential values by one or more different colors mapped upon representations of said surface of said subject's torso.

24. The system as set forth in claim 1, wherein said classifying means further comprises means for determining one or more groups of said P wave data with nearly identical P wave morphology.

25. The system as set forth in claim 24, wherein said determining means uses a statistical analysis for determining said one or more groups of said P wave data with nearly identical P wave morphology.

26. The system as set forth in claim 24, wherein said determining means uses pattern recognition techniques for determining said one or more groups of said P wave data with nearly identical P wave morphology.

27. The system as set forth in claim 24, wherein said determining means uses neural networks for determining said one or more groups of said P wave data with nearly identical P wave morphology.

28. The system as set forth in claim 24, wherein said determining means uses anatomical subdivisions of a heart for determining locations of left atrial ectopic origins.

29. The system as set forth in claim 1, wherein said classifying means further comprises verifying means to verify said P wave data.

30. The system as set forth in claim 29, wherein said verifying means uses statistical analysis techniques to verify said P wave data.

31. The system as set forth in claim 29, wherein said verifying means further comprises means for computing correlation coefficients between said P wave data.

32. The system as set forth in claim 31, wherein said means for computing correlation coefficients further comprises means for assessing intragroup pattern uniformity.

33. The system as set forth in claim 31, wherein said means for computing correlation coefficients further comprises means for assessing intergroup pattern variability.

34. The system as set forth in claim 29, wherein said averaging means further comprises means for calculating mean P wave data from said verified P wave data to construct a database of verified mean P wave data.

35. The system as set forth in claim 1, wherein said averaging means further comprises means for associating said mean P wave data to an ectopic origin in a heart wherein said P wave data is obtained during left atrial pacing or spontaneously occurring or induced left atrial arrhythmias.

36. The system as set forth in claim 35, wherein said associating means uses a schematic diagram of a left atrium.

37. The system as set forth in claim 35, wherein said associating means uses an anatomical diagram of a left atrium.

38. The system as set forth in claim 35, wherein said associating means uses biplane fluoroscopic views of said heart.

39. The system as set forth in claim 1, wherein said storing means further comprises means for using a computer to store, search and analyze said mean P wave data.

40. The system as set forth in claim 39, wherein said storing means further comprises means for using said computer to classify and localize said left atrial arrhythmias.

41. A method for developing a database of body surface ECG P wave data for classification and localization of left atrial arrhythmias wherein said database is derived from P wave data of two or more subjects comprising the steps of:
 (a) receiving said P wave data from a subject;
 (b) classifying said P wave data into classified P wave data;
 (c) averaging said classified P wave data into mean P wave data; and
 (d) storing and accessing said mean P wave data in said database.

42. The method as set forth in claim 41, wherein one of said left atrial arrhythmias is an atrial tachycardia, a focal atrial fibrillation, or an orthodromic AV reentrant tachycardia involving an accessory pathway.

43. The method as set forth in claim 41, wherein said P wave data is in the form of maps.

44. The method as set forth in claim 43, wherein said maps are in the form of integral maps.

45. The method as set forth in claim 43, wherein said maps are in the form of potential maps.

46. The method as set forth in claim 41, further comprises the step of obtaining said P wave data by electrically stimulating a left atrium of said subject using a probe.

47. The method as set forth in claim 46, wherein said P wave data is obtained using a transseptal procedure.

48. The method as set forth in claim 46, wherein said P wave data is obtained using a retrograde aortic procedure.

49. The method as set forth in claim 41, further comprises the step of obtaining said P wave data from spontaneously occurring left atrial arrhythmias.

50. The method as set forth in claim 41, further comprises the step of obtaining said P wave data by inducing left atrial arrhythmias.

51. The method as set forth in claim 41, wherein said step of receiving further comprises the step of sensing heart cycle signals while said subject is spontaneously producing a left atrial arrhythmia, while a left atrial arrhythmia is induced in said subject, or while a left atrial pacing is being performed in said subject.

52. The method as set forth in claim 51, wherein said step of receiving further comprises the step of detecting an electrical heart signal with a plurality of sensors proximate a subject's torso.

53. The method as set forth in claim 52, wherein said step of receiving further comprises the step of separating from said electrical heart signal an atrial signal obscured by a ventricular signal.

54. The method as set forth in claim 52, wherein said step of receiving further comprises the step of selecting at least one reference cycle from among a plurality of heart cycles to determine said P wave data.

55. The method as set forth in claim 54, wherein said step of receiving further comprises the step of selecting a time interval of said reference cycle and comparing signals from said plurality of sensors during said selected time interval.

56. The method as set forth in claim 55, wherein said step of receiving further comprises the step of generating a data matrix by integrating said signals from each sensor location within said selected time interval to define an integral value, and arranging said integral value within said matrix according to locations of said associated sensor locations along a surface of said subject's torso.

57. The method as set forth in claim 56, wherein said step of receiving further comprises the step of computing an integral map over said selected time interval and plotting said data matrix.

58. The method as set forth in claim 57, wherein said step of computing further comprises the step of determining lines of constant integral values, and identifying maps of said P wave data using said lines of constant integral values mapped upon representations of said surface of said subject's torso.

59. The method as set forth in claim 57, wherein said step of computing further comprises the step of representing different integral values by one or more different colors mapped upon representations of said surface of said subject's torso.

60. The method set forth in claim 55, wherein said step of receiving further comprises the step of generating a data matrix of potential signals from each sensor location within said selected time interval to define one or more potential values, and arranging said potential values within said matrix according to locations of said associated sensor locations along said surface of a subject's torso.

61. The method set forth in claim 60, wherein said step of receiving further comprises the step of computing one or more potential maps over said selected time interval and plotting said data matrix.

62. The method as set forth in claim 61, wherein said step of computing further comprises the step of determining lines of constant potential values, and identifying maps of said P wave data using said lines of constant potential values mapped upon representations of said surface of said subject's torso.

63. The method as set forth in claim 61, wherein said step of computing further comprises the step of representing different potential values by one or more different colors mapped upon representations of said surface of said subject's torso.

64. The method as set forth in claim 41, wherein said step of classifying further comprises the step of determining one or more groups of said P wave data with nearly identical P wave morphology.

65. The method as set forth in claim 64, wherein said step of determining further comprises the step of providing a statistical analysis for determining said one or more groups of said P wave data with nearly identical P wave morphology.

66. The method as set forth in claim 64, wherein said step of determining further comprises the step of providing pattern recognition techniques for determining said one or more groups of said P wave data with nearly identical P wave morphology.

67. The method as set forth in claim 64, wherein said step of determining further comprises the step of providing neural networks for determining said one or more groups of said P wave data with nearly identical P wave morphology.

68. The method as set forth in claim 64, wherein said step of determining further comprises the step of providing anatomical subdivisions of a heart for determining locations of left atrial ectopic origins.

69. The method as set forth in claim 41, wherein said step of classifying further comprises the step of verifying to verify said P wave data.

70. The method as set forth in claim 69, wherein said step of verifying further comprises the step of providing statistical analysis techniques to verify said P wave data.

71. The method as set forth in claim 69, wherein said step of verifying further comprises the step of computing correlation coefficients between said P wave data.

72. The method as set forth in claim 71, wherein said step of computing correlation coefficients further comprises the step of assessing intragroup pattern uniformity.

73. The method as set forth in claim 71, wherein said step of computing correlation coefficients further comprises the step of assessing intergroup pattern variability.

74. The system as set forth in claim 69, wherein said step of averaging further comprises the step of calculating mean P wave data from said verified P wave data to construct a database of verified mean P wave data.

75. The method as set forth in claim 41, wherein said step of averaging further comprises the step of associating said mean P wave data to an ectopic origin in a heart wherein said P wave data is obtained during left atrial pacing or spontaneously occurring or induced left atrial arrhythmias.

76. The method as set forth in claim 75, wherein said step of associating further comprises the step of using a schematic diagram of a left atrium.

77. The method as set forth in claim 75, wherein said step of associating further comprises the step of using an anatomical diagram of a left atrium.

78. The method as set forth in claim 75, wherein said step of associating further comprises the step of using biplane fluoroscopic views of said heart.

79. The method as set forth in claim 41, wherein said step of storing further comprises the step of using a computer to store, search and analyze said mean P wave data.

80. The method as set forth in claim 79, wherein said step of storing further comprises the step of using said computer to classify and localize said left atrial arrhythmias.

81. An apparatus for classification and localization of left atrial arrhythmias, comprising:
(a) a signal processor means for receiving electrical signals indicative of a heart's electrical activity from a plurality of torso sites during a left atrial arrhythmia;
(b) a means for receiving said P wave signals to compute one or more data maps of said P wave signals;
(c) a classifying means for classifying said data maps of said left atrial arrhythmia, wherein said data maps are classified based on a comparison of said data maps to a database of mean P wave data maps;
(d) a transformation means for graphically representing said data maps of said left atrial arrhythmia on a torso representation of a subject; and
(e) a localizing means for localizing an origin of said left atrial arrhythmia on a representation of a left atrium based on said classified data map.

82. The apparatus as set forth in claim 81, wherein said left atrial arrhythmia is an atrial tachycardia, a focal atrial fibrillation, or an orthodromic AV reentrant tachycardia involving an accessory pathway.

83. The apparatus as set forth in claim 81, further comprises a QRST subtraction means for removing a ventricular activity superimposed on an atrial activity from said electrical signals, and for outputting one or more P wave signals.

84. The apparatus as set forth in claim 81, wherein said representation is a schematic or an anatomical diagram of said left atrium.

85. The apparatus as set forth in claim 81, wherein said representation is based on using biplane fluoroscopic views of said heart.

86. The apparatus as set forth in claim 81, wherein said data maps are in the form of P wave integral maps.

87. The apparatus as set forth in claim 81, wherein said data maps are in the form of P wave potential maps.

88. The apparatus as set forth in claim 81, further comprises a verifying means for verifying said classified data maps.

89. A database of body surface ECG P wave maps for classification and localization of left atrial arrhythmias generated from P wave data of a plurality of subjects, comprising:
(a) one or more P wave data maps generated by computing, classifying and verifying said P wave data; and
(b) a reference set of map patterns specific to different left atrial ectopic origins for localizing said left atrial arrhythmias.

90. The database as set forth in claim 89, wherein said reference set of map patterns are stored in a computer-readable medium.

91. The database as set forth in claim 89, wherein one of said left atrial arrhythmias is an atrial tachycardia, a focal atrial fibrillation, or an orthodromic AV reentrant tachycardia involving an accessory pathway.

* * * * *